United States Patent [19]

Wechter

[11] Patent Number: 5,190,981
[45] Date of Patent: Mar. 2, 1993

[54] FORMULATION CONTAINING S(+) ENANTIOMER OF FLURBIPROFEN OR KETOPROFEN AND METHOD OF USE FOR ORAL ADMINISTRATION FOR PREVENTION AND TREATMENT OF BONE LOSS ASSOCIATED WITH PERIODONTAL DISEASE

[75] Inventor: William J. Wechter, Redlands, Calif.

[73] Assignee: Sepracor Inc., Marlborough, Mass.

[21] Appl. No.: 705,941

[22] Filed: May 28, 1991

Related U.S. Application Data

[63] Continuation-in-part of Ser. No. 568,220, Aug. 16, 1990, abandoned, which is a continuation-in-part of Ser. No. 395,331, Aug. 17, 1989, abandoned.

[51] Int. Cl.$^5$ .................. A01N 37/10; A61K 31/19
[52] U.S. Cl. ..................... 514/900; 514/901; 514/902; 514/568; 514/570
[58] Field of Search ............... 514/900, 901, 902, 568, 514/570

[56] References Cited

U.S. PATENT DOCUMENTS

| | | | |
|---|---|---|---|
| 4,569,837 | 2/1986 | Suzuki et al. | 514/902 |
| 4,906,670 | 3/1990 | Higashi et al. | 514/773 |
| 4,927,854 | 5/1990 | Sunshine et al. | 514/570 |
| 4,933,172 | 6/1990 | Clark, Jr. et al. | 424/49 |
| 4,975,271 | 12/1990 | Dunn et al. | 424/49 |
| 4,996,209 | 2/1991 | Aoki | 514/263 |

FOREIGN PATENT DOCUMENTS

| | | |
|---|---|---|
| 0137668 | 4/1985 | European Pat. Off. |
| WO87/04618 | 8/1987 | PCT Int'l Appl. |
| WO88/03021 | 5/1988 | PCT Int'l Appl. |
| WO88/04658 | 6/1989 | PCT Int'l Appl. |
| US90/04623 | 11/1990 | PCT Int'l Appl. |

OTHER PUBLICATIONS

Jeffcoat, et al., "Flurbiprofen Treatment of Human Periodontitis: Effect on Alveolar Bone Height and Metabolism", J. Periodont. Res. 23: 381–385 (1988).

*Primary Examiner*—Mukund J. Shah
*Assistant Examiner*—Matthew V. Grumbling
*Attorney, Agent, or Firm*—Hamilton, Brook, Smith & Reynolds

[57] ABSTRACT

A method of reducing bone loss and promoting bone regrowth, once loss has occurred, particularly alveolar bone loss associated wtih periodontal disease, and a composition useful in the method. The method comprises applying to buccal membranes a therapeutically effective quantity of at least one S enantiomer, generally an S(+) enantiomer, of a nonsteroidal anti-inflammatory drug, such as S(+) flurbiprofen or S(+) ketoprofen. The composition is a formulation which is a toothpaste or which is a mouthwash.

7 Claims, No Drawings

FORMULATION CONTAINING S(+) ENANTIOMER OF FLURBIPROFEN OR KETOPROFEN AND METHOD OF USE FOR ORAL ADMINISTRATION FOR PREVENTION AND TREATMENT OF BONE LOSS ASSOCIATED WITH PERIODONTAL DISEASE

RELATED APPLICATIONS

This is a continuation-in-part of U.S. Ser. No. 07/568,220 filed Aug. 16, 1990 now abandoned, which is a continuation-in-part of U.S. Ser. No. 07/395,331 filed Aug. 17, 1989, now abandoned. The teachings of these applications are incorporated herein by reference.

BACKGROUND

Periodontal disease, which includes any abnormality, whether inflammatory or degenerative, of tissue around a tooth, is very common worldwide. For example, the World Health Organization has estimated that even if there were no new periodontal disease, it would take 45 years to treat those people who are affected. In addition, the *Journal of Public Health Dentistry* concluded in 1985 that "more than two out of three patients were affected by periodontal disease." Moos, W.F., *Medical Marketing & Media*, 52–54 (1985). Chronic gingivitis (i.e., inflammation of the gingiva or gums) and chronic destructive periodontitis (i.e., a disease of the connective tissue which attaches a tooth to the alveolar bone, which results in alveolar bone resorption, increasing mobility of the tooth and, ultimately, tooth loss) are two common types of periodontal disease.

Although chronic periodontal disease is so common and known to be caused ultimately by bacteria accumulated on the teeth and under the gingiva, progress in its prevention and treatment has been limited and therapy is still largely unsuccessful. Preventive techniques rely heavily on establishing and maintaining good oral hygiene and therapy of existing periodontal disease includes expensive and ongoing treatments, such as periodontal surgery, which, in many cases, must be carried out often and has not been clearly shown to be effective in arresting alveolar bone loss and preserving teeth. Alveolar bone loss or resorption, which occurs after tooth extraction, is also a serious dental problem which cannot, to date, be successfully treated. A more effective method of preventing or treating alveolar bone loss would be of great value, particularly because of the prevalence of its occurrence.

SUMMARY OF THE INVENTION

The present invention is a method of reducing (decreasing or preventing) bone loss and/or promoting bone regrowth, to replace previously destroyed or lost bone, as well as a composition useful in the method. The present method and composition are particularly useful in the case of alveolar bone loss associated with periodontal disease, bone loss associated with osteoporosis and fracture repair. In the method of the present invention, at least one S enantiomer of a nonsteroidal anti-inflammatory drug, such as S(+)flurbiprofen or S(+) ketoprofen, is administered by application to the buccal membranes to an individual, in whom bone loss is to be prevented, reduced or reversed, in sufficient quantities to produce a systemic effect (adequate blood levels of the drug). In the case in which an individual with periodontal disease is being treated, the present method is also useful in reducing (decreasing or preventing) inflammation or gingivitis. Particularly suitable for use in the present method is a composition which can be used to provide a means by which the S enantiomer of one or more nonsteroidal anti-inflammatory drugs can be applied to make sufficient contact with an individual's buccal membranes to result in adequate blood levels of the drug to produce the desired effect. Typically, the composition will be a formulation, referred to as a toothpaste, but which can be any form (gel, powder, foam) or a mouthwash. The toothpaste is used as is any other toothpaste (typically, it is applied by brushing), as is the mouthwash, with which an individual gargles, rinses his or her mouth, etc.

The composition of the present invention includes at least one S enantiomer, typically the S(+)enantiomer(s), of the nonsteroidal anti-inflammatory drug(s), either in highly purified form (i.e., substantially free of its R(−) form) or in combination with a small quantity of the R(−) form. In addition, the composition includes a flavoring agent or agents and other components typically present in toothpastes (gels, powders, foams, etc.). Because the S(+) enantiomer, which is readily absorbed and is likely to have enhanced bioavailability, is used in the composition, a lower concentration is needed than would be the case if the typically-used racemic mixture were included in the composition. Typically, the nonsteroidal anti-inflammatory drug(s) will be present in the composition in a concentration of approximately 0.1 to approximately 5.0% and preferably in a concentration of approximately 0.25% to approximately 1.0%, although the level can be altered as needed. In the case in which two or more such enantiomers are present, the total concentration falls within this range. The present composition and the method of using it in preventing or treating bone resorption and inflammation secondary to periodontitis and in promoting bone regrowth once it has occurred have several advantages over other formulations or methods of treating this condition. For example, because the active component of the composition is the highly purified S(+) enantiomer of the nonsteroidal anti-inflammatory drug, a relatively low concentration is needed and, thus, the problems of unpleasant or bitter taste and irritation to tissues of the mouth and/or other areas of the gastrointestinal tract associated with consumption of such drugs can be avoided. In addition, because the S(+) enantiomer is well absorbed, it is possible, using such formulations, to produce adequate blood levels (i.e., levels high enough to reduce bone resorption, such as that associated with periodontal disease), reduce inflammation associated with periodontal disease and/or promote regrowth of bone once loss has occurred.

DETAILED DESCRIPTION OF THE INVENTION

The present invention is based on the use of the S enantiomer of at least one nonsteroidal anti-inflammatory agent, typically the S(+) of nonsteroidal anti-inflammatory drugs such as flurbiprofen or ketoprofen, in a composition for oral administration for the treatment and/or prevention of bone resorption.

In one embodiment of the present invention, the S(+) enantiomer of flurbiprofen, of ketoprofen or of another nonsteroidal anti-inflammatory drug which is an aryl propionic acid of sufficient activity to have the desired effect is administered by application to an individual's buccal membranes in order to reduce (decrease or prevent) inflammation and alveolar bone loss associated with periodontal disease and/or to promote bone regrowth associated with the disease. As used herein, the term periodontal disease refers to any disease which affects the periodontia and, typically includes periodontitis, gingivitis and/or periodontosis. The present method can also be used to reduce bone loss associated with other conditions, such as osteoporosis as well as to promote bone regrowth, once loss has occurred. It can also be used in conjunction with fracture repair. In the method of the present invention, the S enantiomer of at least one nonsteroidal anti-inflammatory drug is administered in a highly purified form (i.e., essentially free of its R form or in combination with a small quantity of its R form). The S enantiomer is typically the dextrorotatory enantiomer and is designated S(+) using standard chemical notation. Further description of the present method and composition used therein will refer to the S(+) enantiomer, although it is not to be construed as limiting (i.e., the active enantiomer is what is intended).

In the case in which the S(+) enantiomer-containing composition is administered to treat or prevent alveolar bone loss and/or to promote alveolar bone regrowth associated with periodontal disease, the composition is a formulation, referred to for convenience as a toothpaste, although it may take other forms which can be applied to the gum area by brushing or other means of topical application, or is a mouthwash. The toothpaste may be, for example, a gel, powder, or a foam which is applied to the gums and then removed (e.g., by further or continued brushing with a toothbrush which does not contain the formulation or by rinsing with water). In general, the toothpaste formulation of the present invention contains from approximately 0.1% to 5.0% of the S(+) enantiomer and, preferably, from approximately 0.25% to approximately 1.0% of the S(+) enantiomer in highly purified form, although this concentration can be varied as needed in a particular instance. The toothpaste is applied in sufficient quantity (e.g., 1-2 grams toothpaste, twice daily) and for sufficient time to produce adequate blood levels (an adequate systemic level) to result in the desired effect. It also appears that this results in localized tissue levels which are of value in producing the desired effect.

The S(+) enantiomer of flurbiprofen and the S(+) enantiomer of ketoprofen have been shown to be readily absorbed when taken orally. In general, because these drugs are themselves acids, the composition (toothpaste, mouthwash) should be acidic (e.g., pH of 5.0 to 6.5) to enhance the absorption of the drug(s). The selected S(+) enantiomer can be incorporated into an existing toothpaste formulation, simply by mixing, or can be included with other components as they are combined. An important consideration in terms of user acceptance and willingness to comply with a use regimen is inclusion in the formulation of a flavoring material (e.g., menthol, spearmint, peppermint) sufficiently strong to cover or reduce the flavor of the S(+) enantiomer, which is generally regarded as unpleasant because it is bitter, as well as to reduce the burning sensation it can cause. Because the S(+) enantiomer is used, however, masking or reducing the unpleasant flavor is not as difficult as would be the case if the racemic mixture were used because of the considerably smaller quantity of the S(+) enantiomer used (e.g., approximately one half that of the racemic mixture) and, thus, the lower intensity of the unpleasant flavor. Other aryl propionic acids can be used such as: carprofen, naproxin, indoprofen, pierprofen, pranoprofen, microprofen, thiaoxa and aminoprofen.

In the present method, the S(+) enantiomer-containing formulation is applied in sufficient quantity (e.g., generally 1-2 grams of a 0.25% to 1.0% toothpaste), twice a day. Thus, the amount of S(+) enantiomer that is applied twice daily can range from 1-50 mg, but usually ranges from 2.5-20 mg. Because the S(+) enantiomer of flurbiprofen or of ketoprofen is used and can be incorporated into a formulation which is acceptable to an individual and convenient for self administration/home use, the present method and composition avoid an important limitation of previously-described methods, in which using racemic mixtures (S(+), R(−)) of either or both compound(s) were used and must be administered in tablet or other form which did not remain in the mouth for any length of time. A particular advantage of the present method and formulation is that it can easily be administered on an on-going basis and user compliance will be high.

The ability of a particular (selected) formulation to have the desired effect (i.e., reduce inflammation, reduce bone loss, promote regrowth) can be assessed using standard techniques. For example, its effect on inflammation is determined by observation, to determine whether the redness and/or puffiness or edema characteristic of inflammation has decreased. Bone loss reduction can be assessed using the method of Jeffcoat and co-workers. Jeffcoat, M. K. et al., J. Periodont. Res., 23: 381–385 (1988). As described by Jeffcoat et al., the bone-seeking radiopharmaceutical 99m-Tc-MDP is used to assess the effect of a nonsteroidal anti-inflammatory drug (in the instant case, e.g., S(+) flurbioprofen or S(+) ketoprofen) in reducing periodontal disease activity. As applied to assessment of the effects of the S(+) enantiomers, alveolar bone height is determined using standardized radiography and alveolar bone metabolism is assessed using 99m-Tc uptake prior to administration of the selected S(+) enantiomer and [2] months after administration begins. A reduction in radiopharmaceutical (99m-Tc) uptake, after S(+) enantiomer administration, in the alveolar bone of teeth shown initially (prior to administration) to be undergoing active bone loss is interpreted as an indication that the S(+) enantiomer used has a beneficial effect (i.e., reduces alveolar bone loss in individuals with periodontal disease). Bone regrowth can be assessed using a standard method, such as digital subtractive radiography (see Jeffcoat et al.).

In the embodiment of the present method in which S(+) flurbiprofen or S(+) ketoprofen is administered orally to reduce bone resorption and/or promote bone growth associated with conditions or diseases other than periodontal disease, such as osteoporosis and fracture repair, the selected S(+) enantiomer is applied in a similar manner, resulting in the desired systemic effect (i.e., blood levels appropriate for affecting bone metabolism).

The S enantiomer used in the method and composition of the present invention can be produced by any appropriate method. For example, it can be produced by the method described in WO 89/09765. This patent teaches a combination of organic synthesis and enzymatic treatment to produce the desired enantiomer of drugs such as flurbiprofen or ketoprofen. Alternatively, the S(+) enantiomer of flurbiprofen can be produced by the method described in Example 1 herein.

The following Examples detail the protocols for producing the S(+) enantiomer of flurbiprofen, for formulating a toothpaste as a vehicle for administering S(+) flurbiprofen, and for assessing the bioavailability of toothpastes containing various levels of S(+) flurbiprofen. The bioavailability of S(+) ketoprofen and other S(+) enantiomers can also be determined using this protocol. These Examples are not intended to be limiting of the invention.

EXAMPLES

Example 1

Preparation of S(+) Flurbiprofen

The following is a description of the resolution of flurbiprofen by an enzymatic process. Included is a description of the synthesis of the water-soluble ester used (a two step procedure), as well as the actual enzymatic resolution, subsequent base hydrolysis of the non-substrate ester, and the recovery of both enantiomers of flurbiprofen acid.

A. Synthesis of Flurbiprofen Dimethylethanolamine Ester 0.5 moles (122 g) BP grade racemic flurbiprofen was added to 1.0 moles (73 mls) of SOCl$_2$ in a flask fitted with a drying tube. 250 μl of dimethylformamide was added to the reaction mixture as a catalyst. The reaction mixture was then stirred and warmed gently until the flurbiprofen dissolved and gas evolution commenced. The heat was then removed, and the reaction mixture allowed to stir at 20°-22° C. for 18 hours, after which time the excess SOCl$_2$ was removed under reduced pressure. The remaining material was a liquid which slowly solidified. IR analysis of the liquid indicated total conversion of the carboxylic acid to the acid chloride. 131.0 g of flurbiprofen acid chloride were recovered, indicating a 99.7% conversion. This material was carried on to the next step without any further purification.

The entire quantity of acid chloride was then dissolved in 125 mls of THF, and added dropwise to a solution of 1.0 moles (100.5 mls) of N,N-dimethlethanolamine dissolved in 500 mls of THF in a flask fitted with a drying tube. The addition of the acid chloride solution was made over approximately 60 minutes during which time the reaction mixture was cooled to 0° C. by an ice/water bath. When addition was complete, the ice bath was removed, and the entire mixture allowed to stir at 20° C.-22° C. for 18 hours. The reaction was then worked-up by the careful addition of 500 mls of saturated aqueous K$_2$CO$_3$ solution. The resulting organic layer was separated, and remaining aqueous layer extracted twice with 250 mls of diethyl ether. The organic layers were combined, back-washed with saturated NaCl solution, dried over anhydrous K$_2$CO$_3$, and evaporated under reduced pressure to leave a colourless, viscous oil. 112.0 g of material were recovered, giving a 71% yield. IR analysis of the product indicated only an ester carbonyl function.

B. Quaternization of the N,N-Dimethylethanolamine Ester

The entire quantity of the N,N-Dimethyl-ethanolamine ester (0.355 moles) was dissolved in 500 mls of diethyl ether and stirred in a flask cooled to 0° C. by an ice/water bath. To this solution was added dropwise a solution of 1.0 equivalents (0.355 moles, 33.6 mls) of dimethyl sulphate, dissolved in 100 mls diethyl ether over approximately 60 minutes. The ice bath was then removed, and the reaction mixture allowed to stir at 20° C.-22° C. for 18 hours. The resulting solid material was removed by filtration, washed with diethyl ether and dried under vacuum at 20°-22° C. to leave 156.9 g (100% yield in quaternization step, 70% yield from racemic flurbiprofen acid) of the N,N,N-trimethyl ethanolammonium ester (also known as the choline ester) of flurbiprofen.

C. Enzymatic Hydrolysis of the Racemic Flurbiprofen Choline Ester 75 mmols of the racemic choline ester were dissolved in 1L of 200 mM sodium phosphate buffer at pH 7.0. To this solution was added 2.0 g of a protease derived from *Aspergillus oryzae*, which is available commercially from the Amano Enzyme Company under the name Prozyme 6. The reaction was allowed to stir gently at 20° C.-22° C. for 48 hours. The entire enzymatic reaction mixture was then acidified to a pH of 2 to 3 by the careful addition of concentrated HCl, and the resulting mixture was extracted 3 times with 150 mls of diethyl ether. The ether layers were combined, dried over anhydrous K$_2$CO$_3$, and evaporated under reduced pressure to leave crude (R)-flurbiprofen acid, which was dried under vacuum, and an acidic aqueous solution containing (S)-flurbiprofen choline ester.

The remaining acidic aqueous mixture was then made basic, by the careful addition of NaOH, until the pH had risen to 12.5. The resulting mixture was allowed to stir at 20° C.-22° C. for approximately two hours, after which time the pH was again brought to approximately pH 2 by the careful addition of concentrated HCl in order to precipitate the flurbiprofen acid produced by the base hydrolysis of the choline ester. The resulting mixture was extracted 3 times with 150 mls of diethyl ether. The ether layers were combined, dried over anhydrous K$_2$CO$_3$, and filtered into a clean flask. This solution was chilled to approximately −10° C. in order to crystallize the (S)-flurbiprofen acid. The resulting crystals were collected by filtration, and dried under vacuum.

The enantiomeric excess of each isomer was determined by polarimetry, assuming an $[\alpha]_D$ value of +42.7° (c=1.0, CHCl$_3$) for (S)-flurbiprofen acid of 100% ee.

In order to prepare a reasonable amount of resolved flurbiprofen, the procedures outlined immediately above for the enzymatic hydrolysis of the racemic choline ester substrate, and the subsequent recovery of both the (R)- and (S)-flurbiprofen acid, were repeated exactly as described four times. The (R)- and (S)-acid products were combined to give the following yields of materials;

(R)-flurbiprofen 18.0 g, $[\alpha]_D$= −31.2°, ee=73%

(S)-flurbiprofen 18.0 g, $[\alpha]_D$= +36.7°, ee=86%

Subsequent re-crystallization of the (S)-acid material from ether gave (S)-flurbiprofen of 95% enantiomeric excess.

EXAMPLE 2

Toothpaste Composition

| | |
|---|---|
| S(+) Flurbiprofen | 1.0% |
| Magnesium aluminum silicate | 1.0% |
| Dicalcium phosphate | 47.0% |
| Sodium carboxymethylcellulose | 0.5% |
| Mint flavor | 4.0% |
| Sodium lauryl sulfate | 2.0% |
| Benzoic acid | 0.1% |
| Water | 44.4% |

The nonaqueous ingredients are slowly added to the water with stirring. The resultant mixture is then passed through a roller mill.

EXAMPLE 3

Evaluation of Bioavailability of S(+) Flurbiprofen in Toothpaste

The purpose of this study was to show how well subjects tolerated three strengths of S(+) flurbiprofen toothpaste (1%, 0.5% and 0.25%), as well as the relationship between dose and blood level of the active isomer in comparison with an identical formulation of racemic flurbiprofen (1%) or an intermediate formulation of 80% S(+) flurbiprofen and 20% R(−) flurbiprofen (1%). A toothpaste containing one of the three concentrations of S(+) flurbiprofen, the 1% intermediate formulation or 1% racemic flurbiprofen were used in the study.

The drug is an acid and, therefore, the formulation was adjusted to pH 5.6, in order to improve buccal absorption. The formulation also contained menthol or wintergreen in order to mask the slight bitter taste of the drug. Standard formulation techniques were used.

Eight healthy adult volunteers were selected as subjects for the five-way, blinded, crossover study of flurbiprofen blood levels over a 24 hour period following toothbrushing with toothpastes containing the different concentrations of S(+) flurbiprofen and R(−) flurbiprofen. Each volunteer brushed with about 1 g of a toothpaste formulation for 1 minute followed by rinsing twice daily for 3 days. On the fourth morning, brushing with 1 g of the toothpaste formulation was repeated and blood samples were collected for subsequent analysis at −0.25, 0.25, 1, 2, 4, 8, 12, 23 and 24 hours relative to this toothbrushing episode. Each treatment period was followed by a washout interval of 4 days before the next toothpaste formulation was provided.

The concentration of the individual enantiomers was determined by HPLC on chiral-APG (5μ, 100×4 mm). The mobile phase was 1% 2-propanol in 10 mM $NaH_2PO_4$ buffer, pH 7.0, at 0.6 ml/min. The enantiomers were detected by fluorescence monitoring with excitation at 250 nm and emission at 315 nm. The individual enantiomers were detectable down to 5–10 ng/ml. Standard and calibration curves were prepared for each set of samples and an internal standard of S(+) ibuprofen was added to all samples. Pharmacokinetic calculations were non-compartmental and employed conventional data analysis (linear trapezoidal role) to determine the concentrations or total amounts for each enantiomer and formulation that were analyzed.

The results of this study are presented as follows: 1% by weight racemic flurbiprofen (1S, 1R); 1% by weight 80% S(+) flurbiprofen, 20% R(−) flurbiprofen as a eutectic mixture (2S, 2R); 1% by weight 95% S(+) flurbiprofen, 5% R(−) flurbiprofen (3S); 0.5% by weight 95% S(+) fluriprofen, 5% R(−) flurbiprofen (4S); and 0.25% by weight 95% S(+) flurbiprofen, 5% R(−) flurbiprofen (5S). It should be noted that approximately equivalent amounts (5 mg) of S(+)flurbiprofen were administered in results denoted 1S and 4S. The results from the present study have been further compared with calculations based on results from a previous study by Stalker et al. "Bioavailability of Flurbiprofen following Buccal Administration", Pharm Res. 8, 605–608 (1991). The calculated amounts of administered enantiomer in this previous study are 5 mg buccal S(+) flurbiprofen as a mouthwash (buccal S) or 5 mg PO S(+) flurbiprofen (PO S).

The results of these studies are shown in Table I.

TABLE I

| | Bioavailability of Flurbiprofen Enantiomers | | | | |
|---|---|---|---|---|---|
| Flurbiprofen | Measured Parameters | | | | |
| Group | $\bar{C}_{ss}$ | $\bar{C}_{12}$ | $\bar{C}_{24}$ | $AUC°_{12}$ | $AUC°_{24}$ |
| 1S | 42 | 26 | 23 | 441 | 915 |
| 2S | 80 | 40 | 20 | 1064 | 1553 |
| 3S | 78 | 42 | 30 | 958 | 1365 |
| 4S | 70 | 54 | 23 | 855 | 1302 |
| 5S | 34 | 23 | 11 | 463 | 658 |
| 1R | 43 | 19 | 14 | 504 | 798 |
| 2R | 51 | 13 | 34 | 662 | — |
| buccal S | 8 | 1.2 | 0.05 | 21 | — |
| PO S | 201 | 48 | 3.8 | 202 | — | where $\bar{C}_{ss}$ is the mean study state concentration in ng/ml; $\bar{C}_{12}$ is the mean concentration at 12 hours in ng/ml; $\bar{C}_{24}$ is the mean concentration at 24 hours in ng/ml; $\bar{C}_{24}$ is the mean concentration at 24 hours in ng/ml; $AUC°_{12}$ is the total area under the curve of concentration vs. time from 0 to 12 hr; and $AUC°_{24}$ is the total area under the curve of concentration vs. time from 0 to 24 hr.

These results indicate that there is a dose dependent relationship of plasma concentrations of S(+) flurbiprofen administered as a toothpaste between 0.25% and 0.5% by weight but this response becomes non-linear at 1% by weight. There was no accumulation of either the S(+) or R(−) enantiomers of flurbiprofen so the initial plasma concentrations of each enantiomer were approximately the same from toothpaste formulation to toothpaste formulation (data not shown). The C and AUC data both indicate that the toothpaste route of administration is more effective than mouthwash or PO administration for equivalent amounts of S(+) flurbiprofen (e.g. compare 1S and 4S to buccal S or PO S). That is, the blood concentration of S(+) flurbiprofen is higher and its availability is more persistent when in a toothpaste formulation. Finally, comparison of 1S and 4S indicates that administration of a single enantiomer is more effective than as a racemate in enhancing the bioavailability of that enantiomer (S(+) flurbiprofen). That is, the S(+) enantiomer of flurbiprofen is preferentially absorbed when administered alone in a toothpaste formulation than when administered as a racemic mixture.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

I claim:

1. A composition for application to buccal membranes to achieve enhanced bioavailability to promote bone regrowth and to reduce inflammation and bone resorption associated with periodontal disease, said composition comprising a highly purified S(+) enantiomer of at least one nonsteroidal anti-inflammatory drug selected from the group consisting of S(+) flurbiprofen and S(+) ketoprofen in a pharmaceutically acceptable formulation for application to buccal membranes.

2. A composition of claim 1 wherein the composition includes from approximately 0.1% to approximately 5.0% of the nonsteroidal anti-inflammatory drug.

3. An improved toothpaste to achieve enhanced bioavailability to promote bone regrowth and to reduce inflammation and bone resorption associated with periodontal disease, said toothpaste comprising a highly purified S(+) enantiomer of at least one nonsteroidal anti-inflammatory drug selected from the group consisting of S(+) flurbiprofen and S(+) ketoprofen in a pharmaceutically acceptable toothpaste formulation.

4. A toothpaste of claim 3 comprising from approximately 0.1% to approximately 5.0% nonsteroidal anti-inflammatory drug.

5. An improved mouthwash to achieve enhanced bioavailability to promote bone regrowth and to reduce inflammation and bone resorption associated with periodontal disease, said mouthwash comprising a highly purified S(+) enantiomer of at least one nonsteroidal anti-inflammatory drug selected from the group consisting of S(+) flurbiprofen and S(+) ketoprofen in a pharmaceutically acceptable mouthwash formulation.

6. A method of achieving enhanced bioavailability to promote bone regrowth and to reduce inflammation and bone resorption associated with periodontal disease, alone or in combination in an individual, comprising applying to buccal membranes a therapeutically effective quantity of at least one S(+) enantiomer of a nonsteroidal anti-inflammatory drug selected from the group consisting of S(+) flurbiprofen and S(+) ketoprofen, wherein said applying achieves enhanced bioavailability of said S(+) enantiomer to promote bone regrowth and to reduce inflammation and bone resorption associated with periodontal disease.

7. A method of achieving enhanced bioavailability to promote bone regrowth and to reduce inflammation and bone resorption associated with periodontal disease comprising administering, by brushing of the individual's teeth and gum are, a toothpaste comprising a highly purified S(+) enantiomer of a nonsteroidal anti-inflammatory drug selected from the group consisting of S(+) flurbiprofen and S(+) ketoprofen in a therapeutically effective amount, wherein said administering achieves enhanced bioavailability of said S(+) enantiomer to promote bone regrowth and to reduce bone resorption associated with periodontal disease.

* * * * *

UNITED STATES PATENT AND TRADEMARK OFFICE
CERTIFICATE OF CORRECTION

PATENT NO. : 5,190,981

DATED : March 2, 1993

INVENTOR(S) : William J. Wechter

It is certified that error appears in the above-identified patent and that said Letters Patent is hereby corrected as shown below:

Column 10, claim 7, line 20, after "gum" delete "are," and insert --area,--.

Signed and Sealed this

Sixteenth Day of November, 1993

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,190,981
DATED : March 2, 1993
INVENTOR(S) : William J. Wechter

It is certified that error appears in the above-identified patent and that said Letters Patent is hereby corrected as shown below:

Title page, item [57],
Abstract, line 3: "wtih" should read --with--.

Signed and Sealed this

Eleventh Day of January, 1994

Attest:

BRUCE LEHMAN

Attesting Officer

Commissioner of Patents and Trademarks